US012690912B2

(12) United States Patent
Dancy et al.

(10) Patent No.: US 12,690,912 B2
(45) Date of Patent: Jul. 28, 2026

(54) ELECTROSURGICAL PENCIL WITH SMOKE EVACUATION AND ELECTRODE VISUALIZATION

(71) Applicant: Covidien LP, Mansfield, MA (US)

(72) Inventors: Jenna Dancy, Longmont, CO (US); Stephen G. Harmon, Erie, CO (US); Kelsey S. Fitzgerald, Superior, CO (US); James H. Bodmer, Longmont, CO (US); Jason T. Sanders, Longmont, CO (US); Hannah M. Ginsberg, Westminster, CO (US); Clifford D. Owens, Denver, CO (US); Tony G. Moua, Thornton, CO (US)

(73) Assignee: Covidien LP, Mansfield, MA (US)

( * ) Notice: Subject to any disclaimer, the term of this patent is extended or adjusted under 35 U.S.C. 154(b) by 696 days.

(21) Appl. No.: 17/969,770

(22) Filed: Oct. 20, 2022

(65) Prior Publication Data

US 2024/0180609 A1 Jun. 6, 2024

(51) Int. Cl.
*A61B 18/14* (2006.01)
*A61B 18/00* (2006.01)

(52) U.S. Cl.
CPC ...... *A61B 18/1477* (2013.01); *A61B 18/1402* (2013.01); *A61B 2018/00607* (2013.01); *A61B 2018/00916* (2013.01); *A61B 2218/002* (2013.01); *A61B 2218/008* (2013.01)

(58) Field of Classification Search
CPC ............ A61B 18/1477; A61B 18/1402; A61B 2018/00607; A61B 2018/00916
See application file for complete search history.

(56) References Cited

U.S. PATENT DOCUMENTS

| | | | |
|---|---|---|---|
| 5,234,428 A | 8/1993 | Kaufman | |
| 6,458,125 B1 * | 10/2002 | Cosmescu | ............ A61B 18/042 606/41 |
| 6,702,812 B2 | 3/2004 | Cosmescu | |

(Continued)

FOREIGN PATENT DOCUMENTS

WO          9714364 A1      4/1997

OTHER PUBLICATIONS

Extended European Search Report issued in corresponding application 23204545.0 dated Mar. 15, 2024 (11 pages).

*Primary Examiner* — Michael F Peffley
*Assistant Examiner* — Samantha M Good
(74) *Attorney, Agent, or Firm* — Carter, DeLuca & Farrell, LLP

(57) ABSTRACT

An electrosurgical pencil includes a handle housing defining a fluid lumen and a central longitudinal axis. A nozzle defines a fluid lumen in fluid communication with the fluid lumen defined by the handle housing for evacuating fluid from a surgical site. The nozzle includes a slot configured to receive a nub protruding from the distal end portion of the handle housing to releasably couple the nozzle to the handle housing. An electrode configured to deliver electrosurgical energy to tissue has a proximal portion coupled to the handle housing and a distal portion extending through the fluid lumen defined by the nozzle. At least a portion of the electrode extends distally from a distal end of the nozzle. The electrode defines a central longitudinal axis offset from the central longitudinal axis defined by the handle housing.

19 Claims, 13 Drawing Sheets

(56) References Cited

U.S. PATENT DOCUMENTS

| | | | |
|---|---|---|---|
| 8,414,576 B2 | 4/2013 | Cosmescu | |
| 8,690,872 B2 | 4/2014 | Jayaraj | |
| 9,370,394 B2 | 6/2016 | Jayaraj | |
| 9,375,253 B2 | 6/2016 | Greep et al. | |
| 9,421,353 B2 | 8/2016 | Bernard et al. | |
| 9,687,292 B2 | 6/2017 | Cosmescu | |
| 9,907,621 B2 | 3/2018 | Jayaraj | |
| 10,213,249 B2 | 2/2019 | Cosmescu | |
| 10,765,472 B2 | 9/2020 | Greep et al. | |
| 2006/0264928 A1 | 11/2006 | Kornerup et al. | |
| 2009/0062791 A1* | 3/2009 | Lee | A61B 18/1402 |
| | | | 606/45 |
| 2014/0052131 A1* | 2/2014 | Busch-Madsen | |
| | | | A61B 18/1477 |
| | | | 606/41 |
| 2014/0081086 A1 | 3/2014 | Shvetsov et al. | |
| 2014/0228839 A1 | 8/2014 | Cosmescu | |
| 2014/0276763 A1 | 9/2014 | Greep et al. | |
| 2015/0112323 A1 | 4/2015 | Hagg | |
| 2017/0020599 A1 | 1/2017 | Brooke | |
| 2017/0290628 A1 | 10/2017 | Pepe et al. | |
| 2017/0319264 A1 | 11/2017 | Haupt | |
| 2017/0360499 A1 | 12/2017 | Greep et al. | |
| 2018/0014874 A1 | 1/2018 | Cosmescu | |
| 2018/0014875 A1 | 1/2018 | Cosmescu | |
| 2018/0028255 A1 | 2/2018 | Miller et al. | |
| 2018/0036064 A1 | 2/2018 | Shvetsov et al. | |
| 2018/0147002 A1 | 5/2018 | Fleenor | |
| 2018/0153610 A1 | 6/2018 | Minskoff et al. | |
| 2018/0250071 A1 | 9/2018 | Cosmescu | |
| 2018/0333201 A1 | 11/2018 | Greep et al. | |
| 2019/0009009 A1 | 1/2019 | Minskoff et al. | |
| 2019/0110832 A1 | 4/2019 | Simonsen | |
| 2019/0175250 A1 | 6/2019 | Cosmescu | |
| 2019/0175251 A1 | 6/2019 | Cosmescu | |
| 2020/0113618 A1 | 4/2020 | Cosmescu | |
| 2020/0121383 A1 | 4/2020 | Cosmescu | |
| 2021/0186316 A1* | 6/2021 | Thommen | A61B 1/07 |

* cited by examiner

| Electrode | L1 (A) | Body Front to Electrode Tip (B) | Nozzle Length -Total (C) | Nozzle Length - Mating Face to Front (D) | Nozzle ID (@inlet min) | Nozzle Working Length to TTN Ratio |
|---|---|---|---|---|---|---|
| 2.5 | 0.65 | 1.605 | 1.183 | 0.955 | 0.262 | 1.469 |
| 4 | 0.979 | 2.969 | 2.218 | 1.99 | 0.262 | 2.033 |
| 6.5 | 1.211 | 5.361 | 4.378 | 4.15 | 0.262 | 3.615 |

ES Pencil 200 with 2.5" Electrode

ES Pencil 200 with 4.0" Electrode

ES Pencil 200 with 6.5" Electrode

300

400

ELECTROSURGICAL PENCIL WITH SMOKE EVACUATION AND ELECTRODE VISUALIZATION

FIELD

The disclosure relates to electrosurgical devices. More specifically, the disclosure relates to handheld electrosurgical pencils with smoke evacuation and electrode visualization.

BACKGROUND

Electrosurgical (ES) pencils are used in surgery, typically for cutting tissue and/or for coagulating blood vessels. An ES pencil usually includes a handpiece into which electrodes of various shapes and sizes may be placed. The ES pencil is coupled to an ES generator, such as Medtronic's Valleylab™ FX8 or FT10 generator, which supplies the electrode with a high frequency, typically radio frequency (RF) alternating current. The ES generator may supply various waveforms suitable for achieving various surgical effects, such as cutting, coagulating, blending, spraying, fulgurating, and the like.

While using an ES pencil, surgical smoke is often generated. An effective way to evacuate surgical smoke and/or other fluids from a surgical site is to use an ES pencil with an integrated smoke evacuation nozzle in conjunction with a suction device and an ultra-low penetration air (ULPA) filter. Conventional ES pencils rely on a smoke evacuation nozzle situated near the pencil's electrode, which draws smoke into and through the pencil's body, through a long flexible hose, and finally into a powered suction device. Smoke evacuation nozzles are available either as an integrated part of the ES pencil or as a separate component attached to the ES pencil. However, conventional ES pencils with smoke evacuation nozzles are not constructed to optimize smoke capture and electrode visualization.

SUMMARY

Provided in accordance with aspects of the present disclosure is an electrosurgical pencil. The electrosurgical pencil includes a handle housing defining a fluid lumen and a central longitudinal axis. The electrosurgical pencil also includes a nozzle defining a fluid lumen in fluid communication with the fluid lumen defined by the handle housing for evacuating fluid from a surgical site. The nozzle includes a slot configured to receive a nub protruding from the distal end portion of the handle housing to releasably couple the nozzle to the handle housing. An electrode configured to deliver electrosurgical energy to tissue has a proximal portion coupled to the handle housing and a distal portion extending through the fluid lumen defined by the nozzle. At least a portion of the electrode extends distally from a distal end of the nozzle. The electrode defines a central longitudinal axis offset from the central longitudinal axis defined by the handle housing.

In an aspect of the present disclosure, a ratio between a first length measured between a distal end of the handle housing and the distal end of the nozzle and a second length measured between the distal end of the nozzle and a distal end of the electrode is about 1.469.

In another aspect of the present disclosure, the distal end portion of the handle housing is recessed relative to the rest of the handle housing.

In another aspect of the present disclosure, a length between a distal tip of the electrode and the distal end of the nozzle is about 0.65 inches.

In still another aspect of the present disclosure, the electrode is about 2.5 inches in length.

In yet another aspect of the present disclosure, the fluid lumen defined by the handle housing includes a distal opening in fluid communication with the fluid lumen defined by the nozzle. A ratio between an area of the distal opening and a maximum area of the fluid lumen defined by the nozzle is about 0.28.

In another aspect of the present disclosure, a ratio between a length measured between a distal tip of the electrode and the distal end of the nozzle and an outside diameter of the distal end of the nozzle is about 2.0.

In another aspect of the present disclosure, an inner diameter of the nozzle at the distal end of the nozzle is about 0.304 inches.

In still another aspect of the present disclosure, an outside diameter of the distal end of the nozzle is about 0.322 inches.

In yet another aspect of the present disclosure, the central longitudinal axis defined by the electrode is offset from the central longitudinal axis defined by the handle housing by about 0.042 inches.

In still yet another aspect of the present disclosure, the electrode is received through a collet having a flange disposed within the fluid lumen defined by the nozzle. A ratio between an area of the flange and an area of the fluid lumen defined by the nozzle at the flange is about 0.36.

In another aspect of the present disclosure, at least a portion of the nozzle is formed from a radiopaque material.

In another aspect of the present disclosure, a ratio between a distance by which the central longitudinal axis defined by the electrode is offset from the central longitudinal axis defined by the handle housing and an outside diameter of the distal end of the nozzle is about 0.13.

In yet another aspect of the present disclosure, a length between a distal end of the handle housing and a distal tip of the electrode is about 1.065 inches.

Another electrosurgical pencil provided in accordance with the present disclosure includes a handle housing defining a fluid lumen and a central longitudinal axis. A nozzle is removably coupled to a distal end portion of the handle housing. The nozzle defines a fluid lumen in fluid communication with the fluid lumen defined by the handle housing for evacuating fluid from a surgical site. An electrode configured to deliver electrosurgical energy to tissue extends through the fluid lumen defined by the nozzle. A collet coupled to the handle housing is configured to be removably coupled to the electrode. The collet has a flange disposed within the fluid lumen defined by the nozzle. A ratio between an area of the flange and an area of the fluid lumen defined by the nozzle at the flange is about 0.36. At least one activation button extends from a top side of the handle housing and is configured to control delivery of electrosurgical energy to the electrode. The electrode defines a central longitudinal axis offset from the central longitudinal axis defined by the handle housing toward the top side of the handle housing.

In an aspect of the present disclosure, the fluid lumen defined by the handle housing includes a distal opening in fluid communication with the fluid lumen defined by the nozzle. The distal opening has an area of about 0.0341 inches$^2$.

In another aspect of the present disclosure, a ratio between a first length measured between a distal end of the handle housing and a distal end of the nozzle and a second length measured between the distal end of the nozzle and a distal end of the electrode is about 1.469.

In still another aspect of the present disclosure, a proximal portion of the nozzle includes a slot configured to receive a nub protruding from the distal end portion of the handle housing to releasably couple the nozzle to the handle housing.

In yet another aspect of the present disclosure, a ratio between a distance by which the central longitudinal axis defined by the electrode is offset from the central longitudinal axis defined by the handle housing and an outside diameter of a distal end of the nozzle is about 0.13.

Another electrosurgical pencil provided in accordance with the present disclosure includes a handle housing defining a fluid lumen and a central longitudinal axis. The handle housing has a distal end portion that is recessed relative to the rest of the handle housing. A nozzle is removably coupled to the recessed distal end portion of the handle housing. The nozzle defines a fluid lumen in fluid communication with the fluid lumen defined by the handle housing for evacuating fluid from a surgical site. The nozzle has a proximal end portion defining a slot configured to receive a nub protruding from an outer surface of the recessed distal portion of the handle housing to removably couple the nozzle to the handle housing. An electrode configured to deliver electrosurgical energy to tissue has a proximal portion coupled to the handle housing and a distal portion extending through the fluid lumen defined by the nozzle. At least a portion of the electrode extends distally from a distal end of the nozzle.

BRIEF DESCRIPTION OF THE DRAWINGS

Aspects of the disclosure are described herein with reference to the accompanying drawings, wherein.

DETAILED DESCRIPTION

Figure 1:
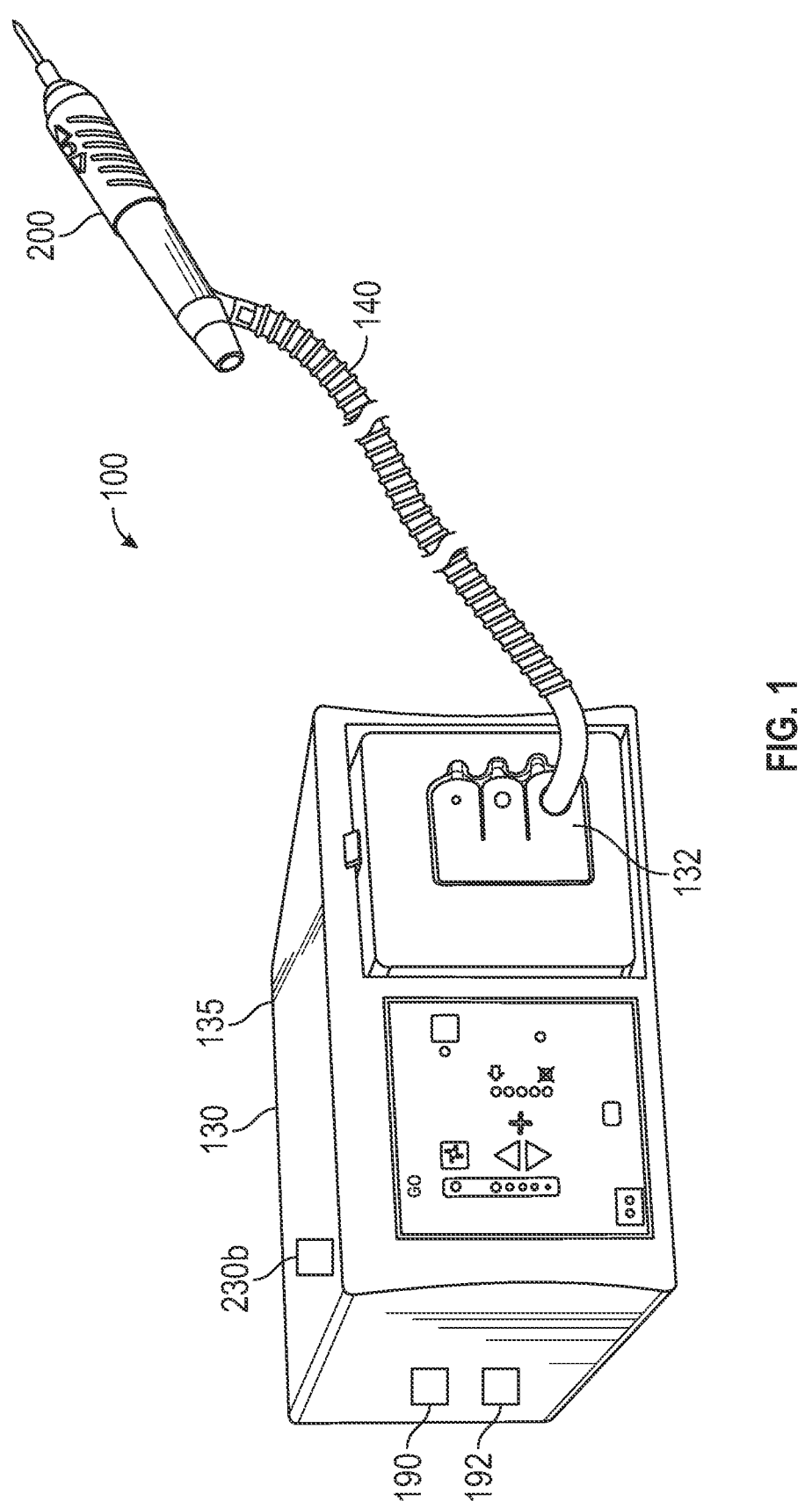
FIG. 1 is a perspective view of a surgical smoke evacuation system, in accordance with aspects of the disclosure.
Figure 2:
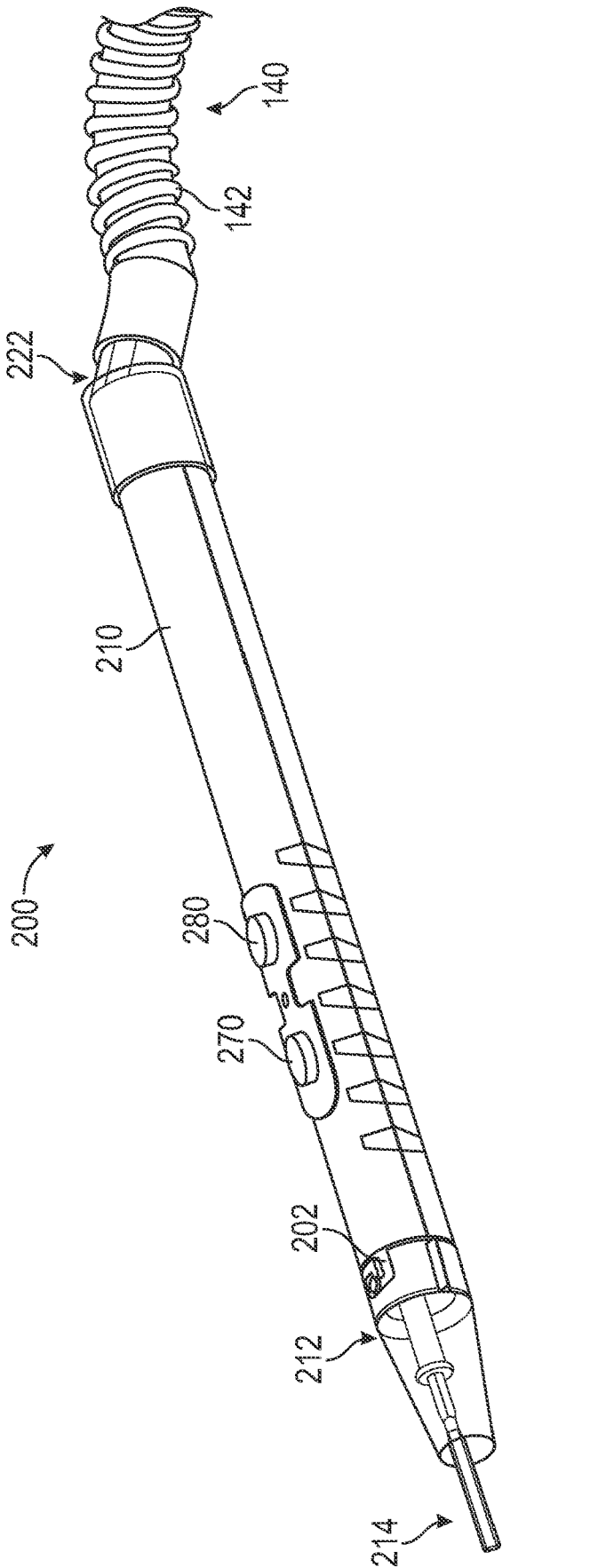
FIG. 2 is a side perspective view of an electrosurgical (ES) pencil of the surgical smoke evacuation system of FIG. 1, in accordance with aspects of the disclosure.

Embodiments of the disclosure are now described in detail with reference to the drawings in which like reference numerals designate identical or corresponding elements in each of the drawings. The aspects may be combined in any manner consistent with the functionality of the apparatus and/or method disclosed herein. As used herein, the term "clinician" refers to a doctor, a surgeon, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. As used herein, the term "exemplary" does not necessarily mean "preferred" and may simply refer to an example unless the context clearly indicates otherwise.

Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent.

Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the disclosure in unnecessary detail.

Figure 3:
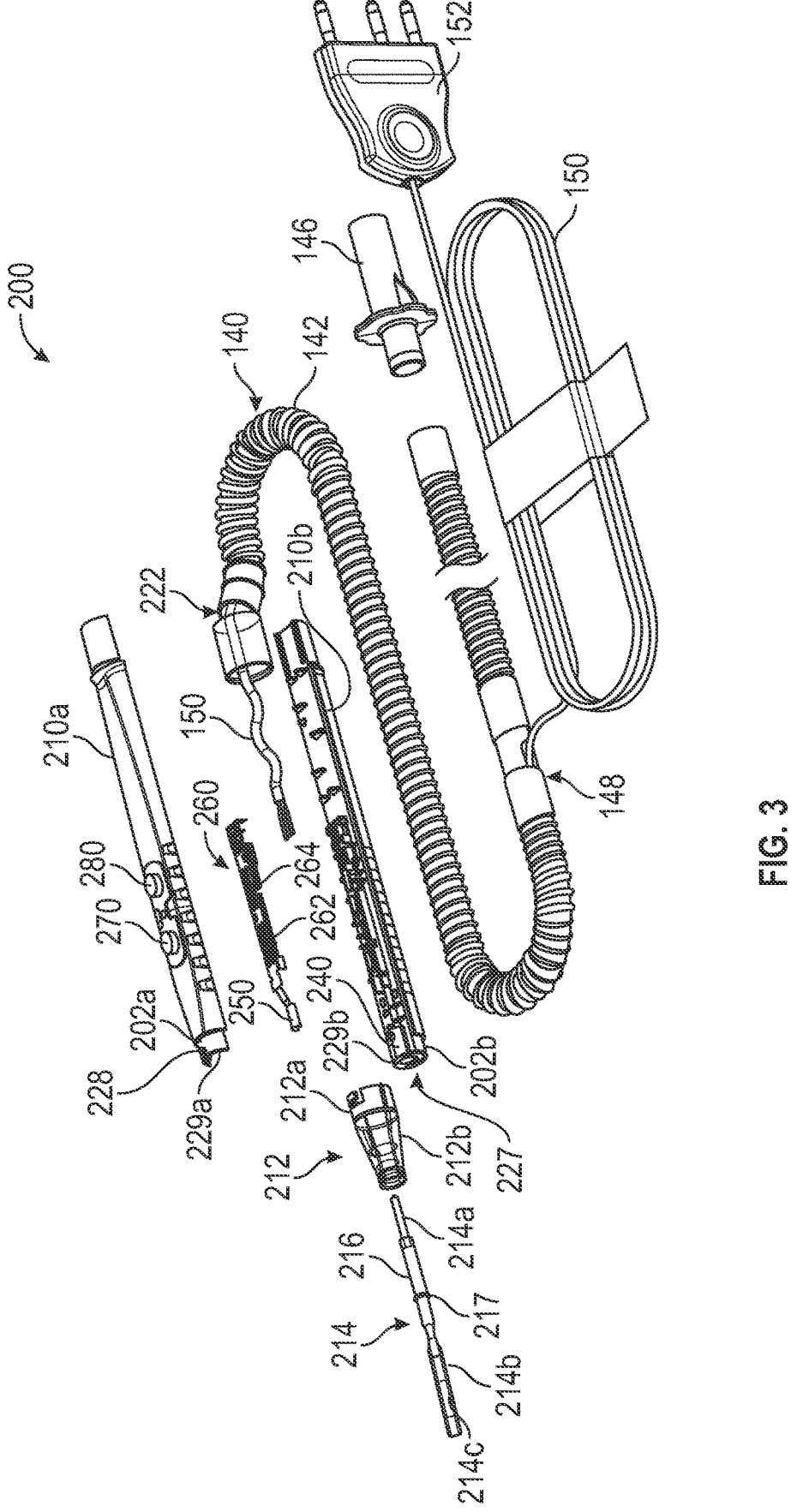
FIG. 3 is an exploded perspective view of the ES pencil of FIG. 2, in accordance with aspects of the disclosure.

This disclosure relates to an ES pencil that is constructed to effectively accomplish smoke capture and electrode visualization during operation of the ES pencil to treat tissue and evacuate fluid (e.g., surgical smoke, debris, gaseous byproducts, etc.) from the surgical site. With reference to FIGS. 1-4B, a surgical smoke evacuation system 100 in accordance with aspects of this disclosure is shown. The surgical smoke evacuation system 100 generally includes a smoke evacuator 130, an ES pencil 200 having a handle housing 210, and tubing 140 connecting the ES pencil 200 to the smoke evacuator 130. The handle housing 210 may be configured as a handle configured to be gripped by a clinician, although non-handle configurations are also contemplated, e.g., for mounting the ES pencil 200 and/or attaching the ES pencil 200 to a surgical robot arm (see FIG. 19). The smoke evacuator 130 includes a suction generator 135 that creates negative pressure having a vacuum force for removing surgical smoke and/or debris during a surgical procedure. The suction generator 135 may include one or more fans and/or pumps to create negative pressure for enabling smoke removal from a surgical site. A connector 222 (e.g., swivel connector) at a distal end of the tubing 140 couples the handle housing 210 to the tubing 140. A proximal end 144 of the tubing 140 is configured for connection to an inlet port 132 of the smoke evacuator 130. Optionally, the proximal end 144 of the tubing 140 may couple to an adapter 146 (FIG. 3) configured to accommodate connection of the tubing 140 to various sized inlet ports of the smoke evacuator 130. The tubing 140 is in fluid communication with a fluid lumen 225 (FIG. 7), e.g., a smoke lumen, extending through the handle housing 210 of the ES pencil 200. The fluid lumen 225 of the handle housing 210 may be defined by the handle housing 210 itself or, in some aspects, may be a separate tube or luminal structure disposed within the handle housing 210 or coupled to an exterior of the handle housing 210. The tubing 140 may be corrugated by including a spiral spine 142 (FIG. 2) disposed on an outer surface of the tubing 140. The corrugated structure of the tubing 140 minimizes kinking and provides increased flexibility to the tubing 140. As shown in FIG. 3, the tubing 140 may also include an opening 148 at any point along its length for passage of an electrosurgical cable 150 into a lumen defined within the tubing 140. The cable 150 includes a proximal connector 152 (FIG. 3) configured for connection to an electrosurgical generator (not shown). A lumen defined through connector 222 is in fluid communication with the lumen defined through the tubing 140 and the fluid lumen 225 of the handle housing 210. Thus, the fluid lumen 225 of the handle housing 210 is configured to be in fluid communication with the inlet port 132 of the smoke evacuator 130 via the connector 222 and the tubing 140 for evacuating fluid such as, e.g., surgical smoke from a surgical site.

The smoke evacuator 130 also includes a processor 190 and a memory 192. Instructions may be executed by the processor 190, which may include one or more digital signal processors (DSPs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structures or any other physical structure suitable for implementation of the described techniques. Also, the techniques could be fully implemented in one or more circuits or logic elements. It is contemplated that the processor 190 and memory 192 may be located in the smoke evacuator 130, the ES pencil 200, and/or in a remote computer system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Referring to FIGS. 2-4B, the handle housing 210 of the ES pencil 200 defines a central longitudinal axis X1 and is formed from a thermoplastic material. The handle housing 210 includes a first housing portion 210a and a second housing portion 210b, which are secured to each other using any suitable method (e.g., ultrasonic welding) to secure and house internal components of the ES pencil 200. As shown in FIG. 3, the first and second housing portions 210a, 210b include respective recessed distal end portions 202a, 202b

(hereinafter referred to in combination as the recessed distal end portion 202) that terminate at respective distal ends 229a, 229b (hereinafter referred to in combination as the distal end 229).

Figure 4A:
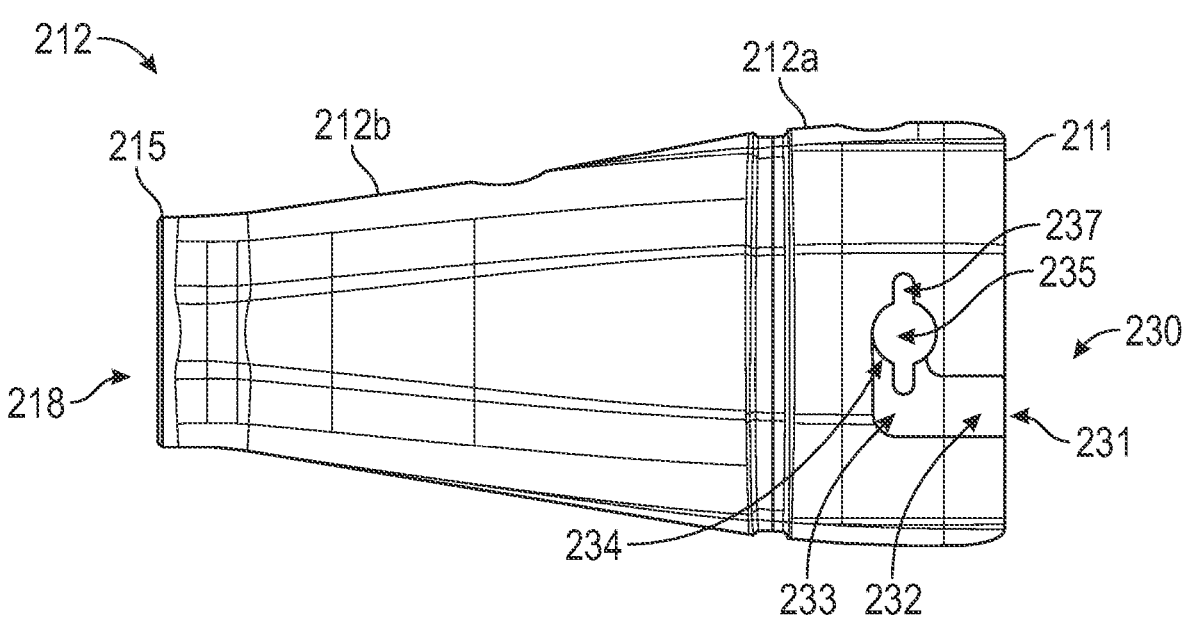
FIG. 4A is a side view of a nozzle of the ES pencil of FIG. 2, in accordance with aspects of the disclosure.

The ES pencil 200 also includes a nozzle 212 extending between a proximal end 211 and a distal end 215 (FIG. 4A). The nozzle 212 includes a proximal portion 212a that serves to removably couple the nozzle 212 to the recessed distal end portion 202 of the handle housing 210 and a distal portion 212b extending distally from the recessed distal end portion 202 of the handle housing 210. A fluid lumen 220, e.g., a smoke lumen, is defined through the proximal and distal portions 212a, 212b of the nozzle 212 for suctioning fluid (e.g., surgical smoke, debris, gaseous byproducts, etc.) from a surgical site through a distal opening 218 of the nozzle 212. The fluid lumen 225 of the handle housing 210 is placed in fluid communication with the fluid lumen 220 of the nozzle 212 by a distal opening 227 (FIG. 3) of the fluid lumen 225 defined at the distal end 229 of the second housing portion 210b. The distal opening 227 serves as a fluid intake to enable fluid (e.g., smoke) suctioned through the nozzle 212 to be evacuated through the handle housing 210 and the tubing 140 via operation of the smoke evacuator 130. In aspects of this disclosure, the distal portion 212b of the nozzle 212 may be a transparent, substantially transparent, or translucent material configured to facilitate visual acuity in the surgical field. For example, the distal portion 212b of the nozzle 212 may be formed from a clear polycarbonate resin. Other resin materials from which to form the distal portion 212b of the nozzle 212 are contemplated such as, for example, polymethylmethacrylate or acrylic (PMMA), polymethylmethyacrylimide (PMMI), silicon-based resins, or the like. In aspects of this disclosure, the proximal portion 212a of the nozzle 212 may be formed from a radiopaque material such as, for example, a thermoplastic polyurethane (TPU) material so that the proximal portion 212a of the nozzle 212 appears opaque under medical imaging modalities that use radiation such as X-rays for example.

The ES pencil 200 includes an electrode 214 extending distally from the recessed distal end portion 202 of the handle housing 210. The electrode 214 includes a distal portion 214a having a tissue treatment portion (e.g., a blade (as shown), a hook, a needle, etc.) and a proximal portion 214a disposed within the handle housing 210. The electrode 214 is removably received through a collet 216 that is, in turn, supported through a receptacle 240 formed within the handle housing 210 (FIG. 3) such that the collet 216 and the distal portion 214b of the electrode 214 extend distally from the recessed distal end portion 202 and through the fluid lumen 220 of the nozzle 212.

In aspects, the electrode 214 is removable from the collet 216 such that the electrode 214 may be replaced by a new electrode and/or by an electrode having a different shape, size, and/or configuration depending on the needs of the clinician for a given procedure. The collet 216 includes a rounded distal electrode flange 217 defining an opening 217a (FIG. 8) through which the electrode 214 is received to removably couple the electrode 214 to the collet 216. As detailed below, the nozzle 212 may also be removable from the handle housing 210 such that the nozzle 212 may be replaced by a new nozzle and/or by a nozzle having a different shape, size, and/or configuration. For example, a nozzle may be replaced with a different size nozzle depending on the size of the electrode being used.

Figure 4B:
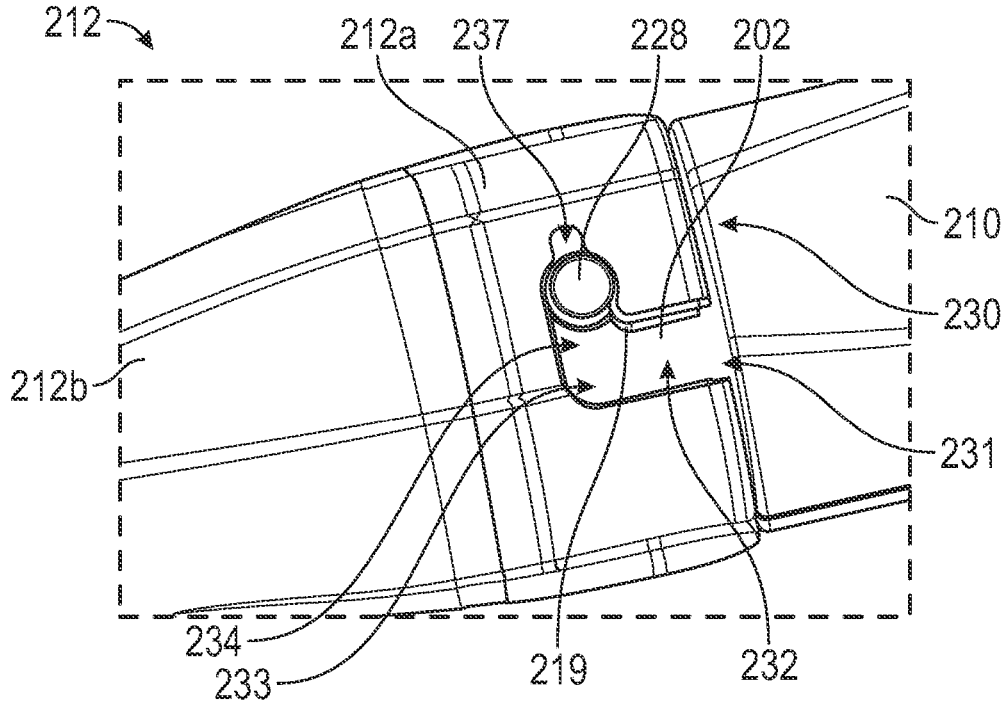
FIG. 4B is a side perspective view of a portion of the nozzle of FIG. 4A removably coupled to a distal end portion of the ES pencil of FIG. 2, in accordance with aspects of the disclosure.
Figure 5:
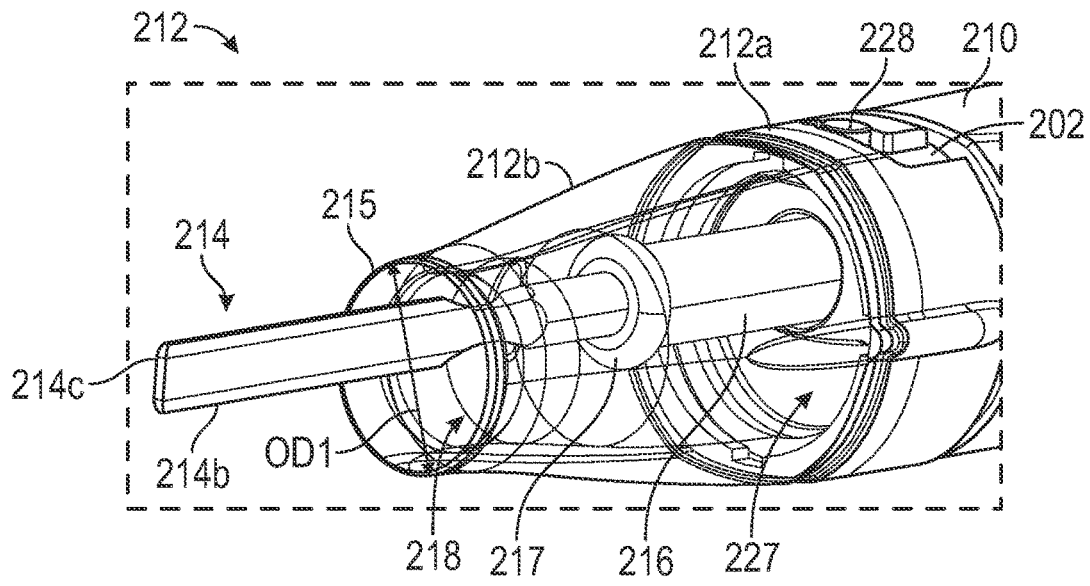
FIG. 5 is a front perspective view of a portion of the ES pencil of FIG. 2, in accordance with aspects of the disclosure.

With reference to FIGS. 4A and 4B, to facilitate removable coupling of the nozzle 212 to the recessed distal end portion 202 of the handle housing 210, the recessed distal end portion 202 of the handle housing 210 includes a nub 228 that protrudes from an outer surface of the recessed distal end portion 202 and is configured to be received within a slot 230 defined by the proximal portion 212a of the nozzle 212. The slot 230 includes a longitudinal segment 232 extending between an open proximal end 231 and a distal end 233. The distal end 233 is in communication with a latitudinal segment 234 extending laterally from the longitudinal segment 232. The latitudinal segment 234 defines a locking portion 235 configured to receive the nub 228 in a removably locking engagement to secure the nozzle 212 to the recessed distal end portion 202 of the handle housing 210. Bridging the longitudinal segment 232 with the locking portion 235 is a rounded retention surface 219. To couple the nozzle 212 to the handle housing 210, the distal end 229 of the handle housing 210 is received within the proximal portion 212a of the nozzle 212 and the nub 228 is received through the open proximal end 231 of the longitudinal segment 232. The nub 228 is caused to traverse along the longitudinal segment 232 toward its distal end 233. Once at or near the distal end 233 of the longitudinal segment 232, the nub 228 is caused to traverse along the latitudinal segment 234 past the rounded retention surface 219 toward the locking portion 235 of the latitudinal segment 234. Traversal of the nub 228 along the latitudinal segment 234 may be caused by rotation of the nozzle 212 relative to the handle housing 212 (or rotation of the handle housing 210 relative to the nozzle 212) about the central longitudinal axis "X1" defined by the handle housing 210. Once the nub 228 moves past the rounded retention surface 219 and comes to a rest within the locking portion 235 as shown in FIG. 4B, the nub 228 is friction fit into the locking portion 235 and the rounded retention surface 219 serves to maintain the nub 228 within the locking portion 235 until such time that the nozzle 212 is to be uncoupled from the handle housing 210. In communication with the locking portion 234 is a stress relief slot 237 configured to limit the stress concentration on the locking portion 234 when the nub 228 is disposed within the locking portion 234. Removal of the nozzle 212 from the handle housing 210 may be achieved by moving the nub 228 through the slot 230 in the reverse order of what is described above with respect to coupling the nozzle 212 to the handle housing 210. Although not explicitly depicted in the figures, the nozzle 212 may include an additional slot disposed opposite to the slot 230 (e.g., a mirror image) that is configured to receive a nub disposed on the recessed distal end portion 202 opposite to the nub 228.

The proximal portion 214b of the electrode 214 extends proximally from the receptacle 240 and is received within an electrically conductive electrode clip 250 of an electrical unit 260 (FIG. 3) disposed within the handle housing 210. In aspects, the electrical unit 260 may be coupled to an interior surface (e.g., ribbing) of the handle housing 210 to secure and stabilize the proximal portion 214b of the electrode 214 within the handle housing 210. The electrical unit 260 is electromechanically coupled to the cable 150, which interconnects the electrical unit 260 to an electrosurgical generator (not shown). The electrical unit 260 includes a pair of switches 262, 264 (FIG. 3), which are aligned with a pair of push buttons 270, 280, respectively, extending from the handle housing 210, thereby allowing for activation of the switches 262, 264 when the corresponding button 270, 280 is pressed. Activation and/or deactivation of pushbutton switches 262, 264 serves to control delivery of electrosurgical energy to the electrode 214. For example, one of the buttons 270, 280 may serve to cause the electrosurgical generator to provide a signal to the electrode 214 for cutting tissue and the other of the buttons 270, 280 may serve to cause the electrosurgical generator to provide a signal to the electrode 214 for coagulating tissue.

In aspects of the disclosure, the buttons 270, 280 may be replaced by any suitable actuation mechanism, such as a rocker switch, a pressure sensitive transducer, or a slider configured to be actuated longitudinally (e.g., distally and proximally) along the handle housing 210.

Described below with reference to FIGS. 5-15 are specific dimensions and geometries of the ES pencil 200 that provide unexpectedly superior performance of the ES pencil 200 with respect to smoke capture and/or electrode visualization. For each of the examples shown in FIGS. 5-15, an outside diameter OD1 (FIG. 5) of the distal end 215 of the nozzle 212 is about 0.322 inches. For each of the examples shown in FIGS. 5-12B, the length of the electrode 214 is about 2.5 inches. However, other lengths of the electrode 214 are contemplated including, but not limited to, about 4.0 inches and about 6.5 inches, as detailed below with reference to FIGS. 13-15. The below-described geometries of the ES pencil 200 have been shown, through rigorous smoke capture testing, to provide unexpectedly superior electrode visualization and smoke capture performance of the ES pencil 200.

Figure 6:
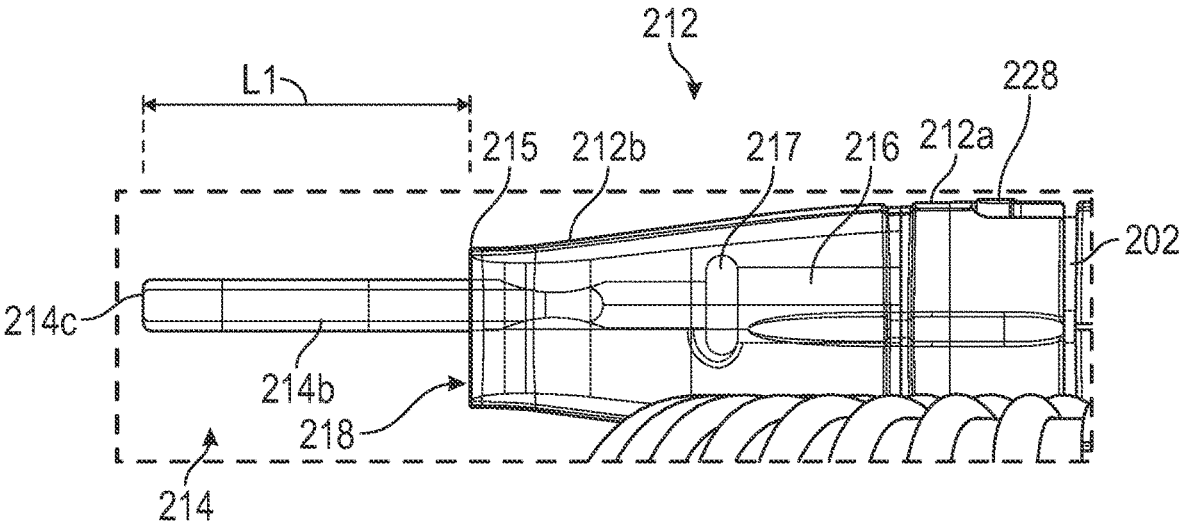
FIG. 6 is a side view of a portion of the ES pencil of FIG. 2, in accordance with aspects of the disclosure.

Referring now to FIG. 6, the electrode 214 is shown extending distally past the distal end 215 of the nozzle 212 to expose at least a portion of the electrode 214 from the nozzle 212. The length L1 of the electrode 214 that extends distally past the distal end 215 of the nozzle is measured between a distal tip 214c of the electrode 214 and the distal end 215 of the nozzle 212. In the example shown in FIG. 6, the length L1 is about 0.65 inches. Thus, a ratio of L1:OD1 (e.g., 0.65/0.322) gives a value of 2.0.

Figure 7:
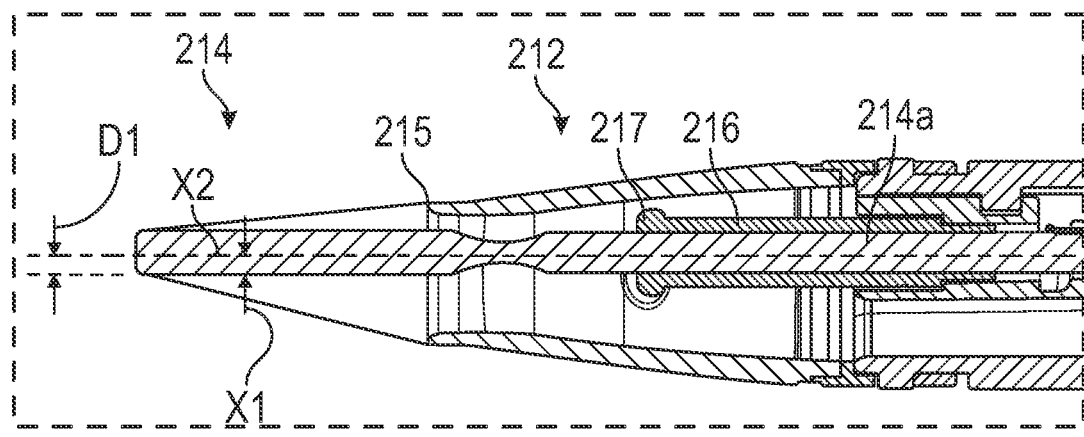
FIGS. 7 and 8 are cross-sectional side views of a portion of the ES pencil of FIG. 2, in accordance with aspects of the disclosure.

Referring now to FIG. 7, the electrode 214 is offset from the central longitudinal axis X1 defined by the handle housing 210 towards the top of the ES pencil 200 to enhance electrode visibility and to maximize the area of the distal opening 227 of the fluid lumen 225 for improving smoke evacuation performance. In this instance, the top of the ES pencil 200 is considered to be the side of the ES pencil 200 that includes the buttons 270, 280 (see FIGS. 2 and 3). As shown in FIG. 7, the electrode 214 defines a central longitudinal axis X2 that is offset toward the top of the ES pencil 200 from the central longitudinal axis X1 defined by the handle housing 210 by a distance D1. In the example shown in FIG. 7, the distance D1 is about 0.042 inches. Thus, a ratio of D1:OD1 (e.g., 0.042/0.322) gives a value of 0.13.

Figure 8:
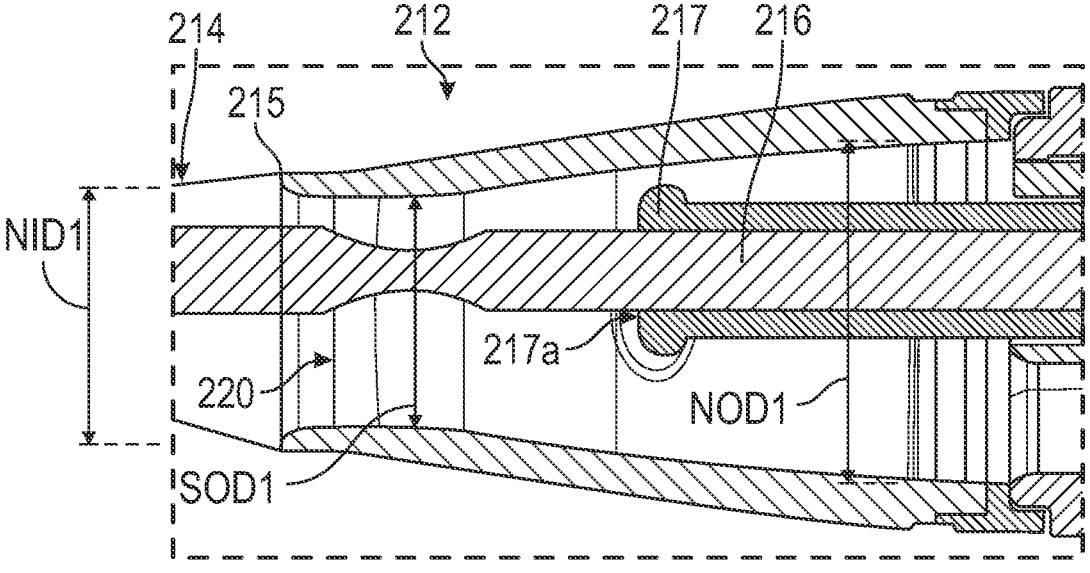

Referring now to FIG. 8, the nozzle 212 includes a nozzle intake diameter NID1 measured within the inner surface of the nozzle 212 at the distal end 215 of the nozzle 212. The nozzle 212 also includes a nozzle outlet diameter NOD1 measured within the inner surface of the nozzle 212 at a proximal end of the nozzle 212 where the fluid lumen 220 defined through the nozzle 212 fluidly communicates with the fluid lumen 225 defined through the handle housing 210. In the example shown in FIG. 8, the nozzle intake diameter NID1 is about 0.304 inches, and the nozzle outlet diameter is about 0.395 inches. Thus, a ratio of NID1:NOD1 (e.g., 0.304/0.395) gives a value of 0.77. Also illustrated in FIG. 8 is a shutoff diameter SOD1 of the nozzle 212, which is measured within the inner surface of the nozzle 212 where the inside diameter of the distal portion 212b of the nozzle 212 is at a minimum. In the example shown in FIG. 8, the shutoff diameter SOD1 is about 0.262 inches.

Figure 9:
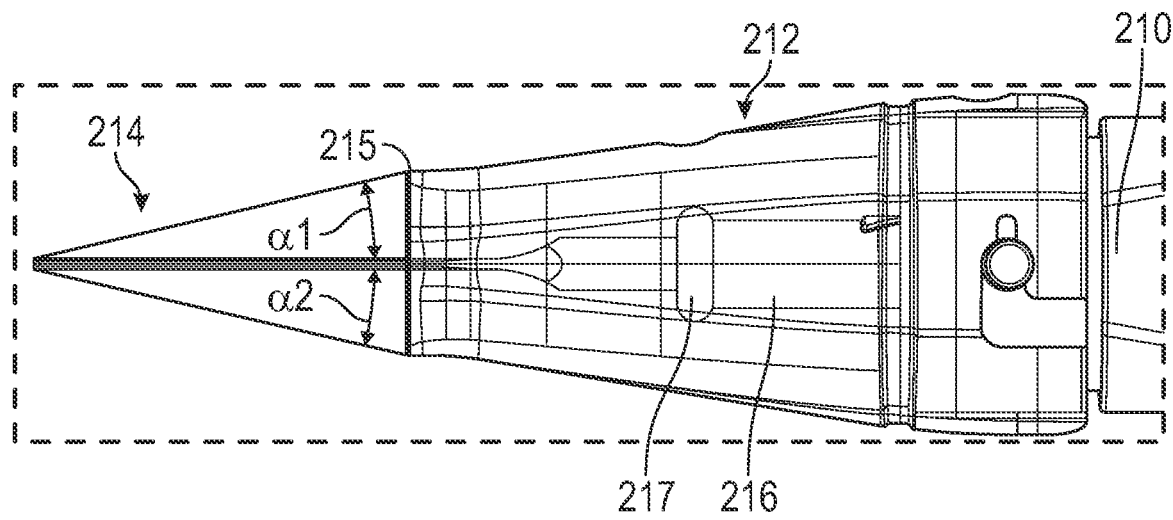
FIGS. 9 and 10 are side views of a portion of the ES pencil of FIG. 2, in accordance with aspects of the disclosure.
Figure 10:
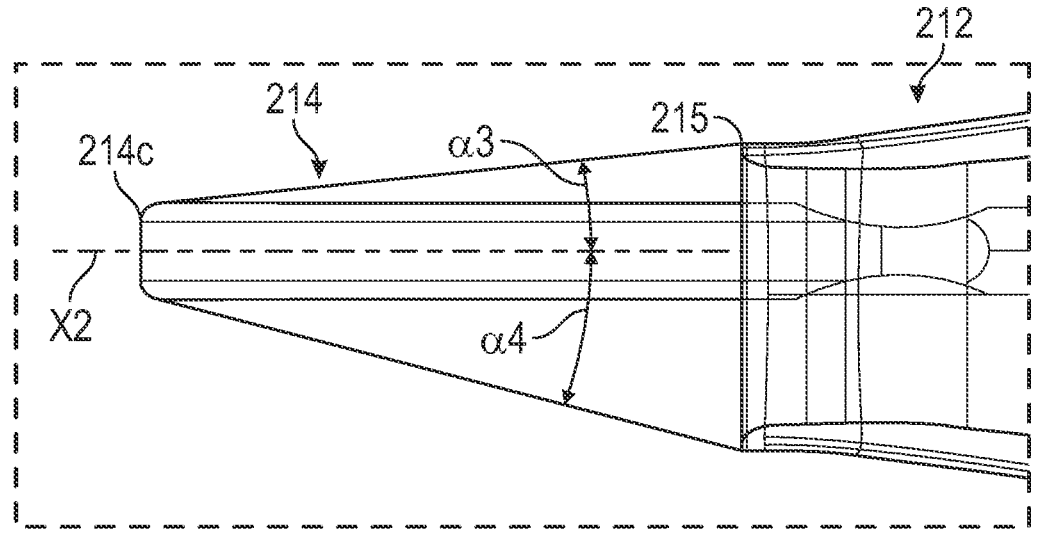

Referring now to FIGS. 9 and 10, respective top and side views of the nozzle 212 and the electrode 214 are shown.

FIG. 9 shows a top view of the nozzle 212 and the electrode 214 to illustrate first and second angles α1, α2 measured from the distal tip 214c of the electrode 214 to opposing lateral sides of the distal end 215 of the nozzle 212. In the example shown in FIG. 9, the first and second angles α1, α2 are equivalent and are about 13 degrees. In another specific example, the first and second angles α1, α2 are equivalent and are about 12.94 degrees. FIG. 10 shows a side view of the nozzle 212 and the electrode 214 to illustrate third and fourth angles α3, α4 measured from the central longitudinal axis X2 defined by the electrode 214 at the distal tip 214c of the electrode 214 to opposing lateral sides of the distal end 215. More specifically, the third angle α3 is measured from the central longitudinal axis X2 at the distal tip 214c to an electrode-biased side of the distal end 215 of the nozzle 212 and the fourth angle α4 is measured from the central longitudinal axis X2 at the distal tip 214c of the electrode 214 to a side of the distal end 215 that is opposite to the electrode-biased side. In the example shown in FIG. 10, the third angle α3 is about 5.40 degrees and the fourth angle α4 is about 13.60 degrees.

Figure 11A:
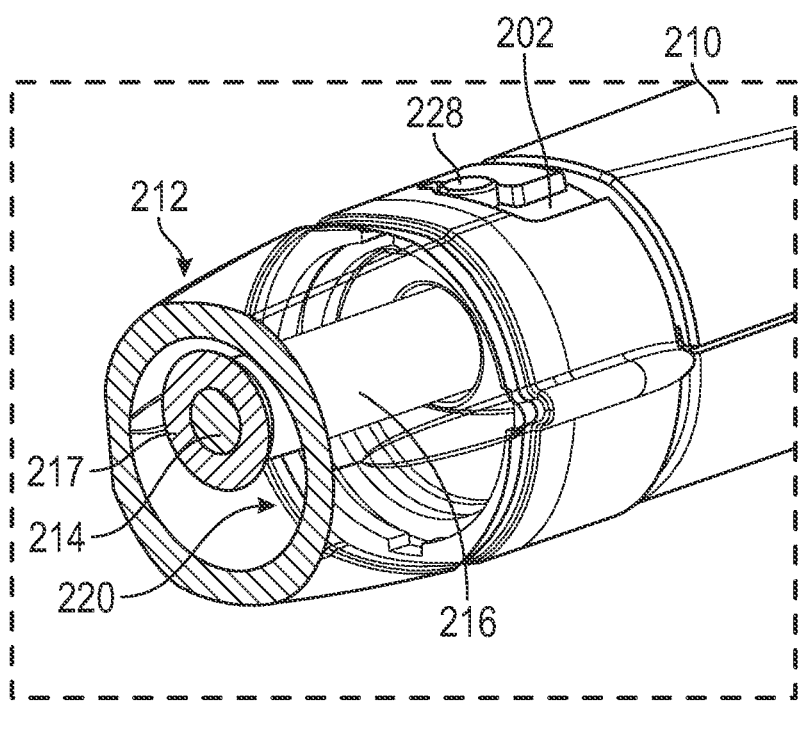
FIG. 11A is a front perspective view of a portion of the ES pencil of FIG. 2 with portions removed, in accordance with aspects of the disclosure.
Figure 11B:
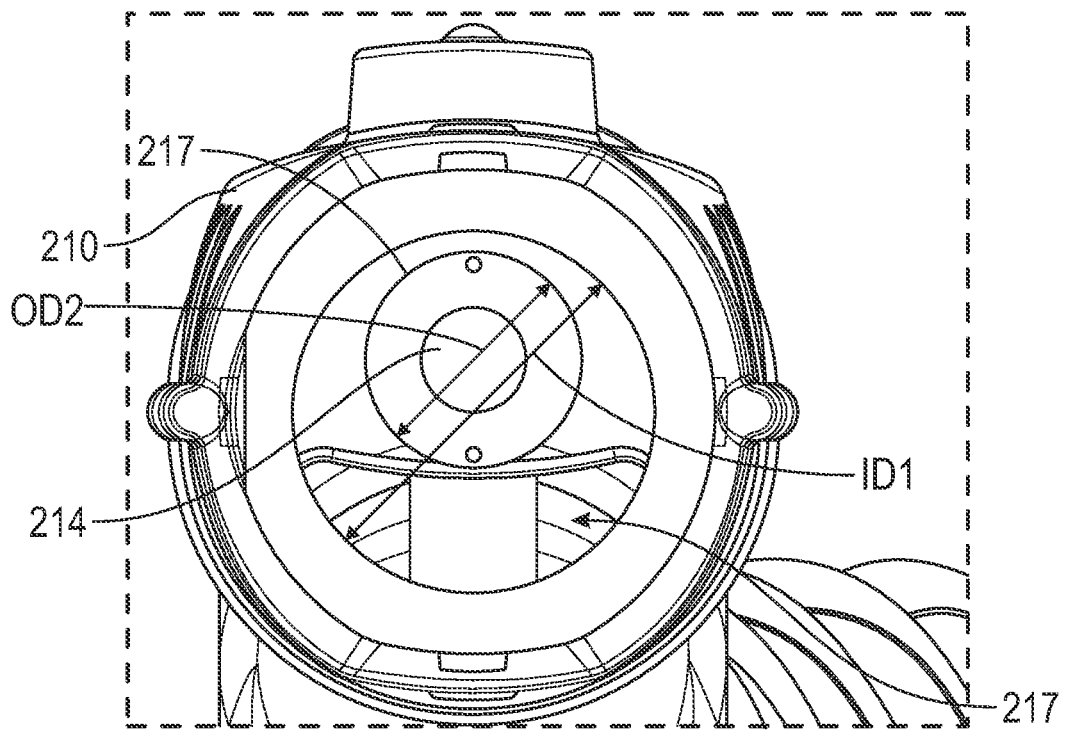
FIG. 11B is a front view of the portion of the ES pencil as depicted in FIG. 11A, in accordance with aspects of the disclosure.

Referring now to FIGS. 11A and 11B, a front perspective view of the ES pencil 200 is shown in FIG. 11A with portions of the electrode 214 removed and portions of the nozzle 212 removed. FIG. 11B shows a front view of the ES pencil 200 as depicted in FIG. 11A to illustrate an outside diameter OD2 of the electrode flange 217 and an inside diameter ID1 of the distal portion 212b of the nozzle 212 measured within the fluid lumen 220 between inner surfaces of the nozzle 212 at the electrode flange 217. In the example of FIG. 11, the outside diameter OD2 is about 0.200 inches and the inside diameter ID1 is about 0.333 inches. Using a value of 0.333 inches for the inside diameter ID1, the total area of the fluid lumen 220 at the electrode flange 217 can be determined by the equation $0.314(0.333/2)^2$, which gives a result of 0.00870 inches$^2$. Using a value of 0.200 inches for the outside diameter OD2, the area of the electrode flange 217 can be determined by the equation $0.314(0.200/2)^2$, which gives a result of 0.00314 inches$^2$. Thus, accounting for the area of the electrode flange 217 occupying a portion of the total area of the fluid lumen 220, a ratio of OD2:ID1-OD2 (e.g., 0.00314/(0.00870–0.00314)) gives a value of 0.56. Without accounting for the for the area of the electrode flange 217 occupying a portion of the total area of the fluid lumen 220, a ratio of OD2:ID1 (e.g., 0.00314/0.00870) gives a value of 0.36.

Figure 12A:
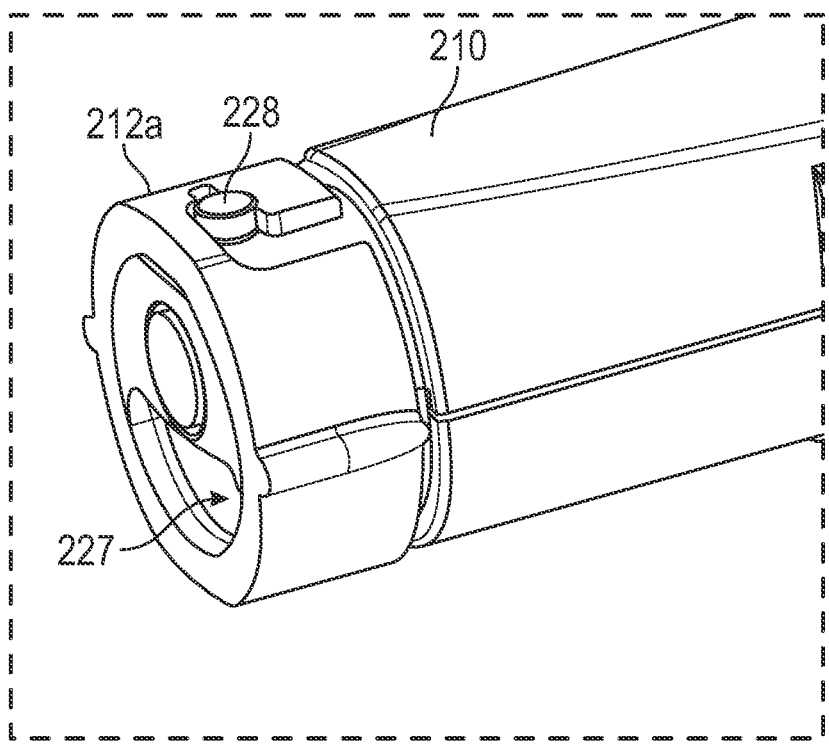
FIG. 12A is a front view of a portion of the ES pencil of FIG. 2 with portions removed, in accordance with aspects of the disclosure.
Figure 12B:
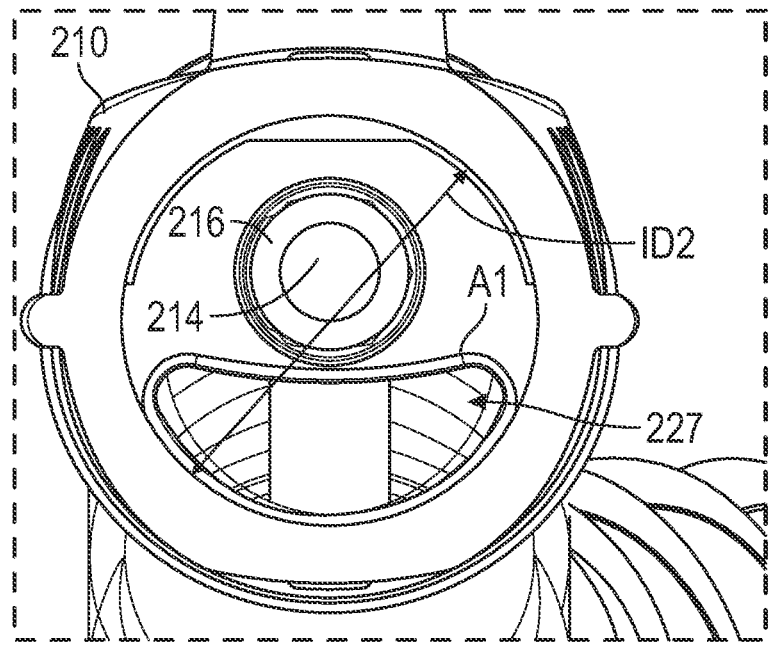
FIG. 12B is a front view of the portion of the ES pencil as depicted in FIG. 12A, in accordance with aspects of the disclosure.

Referring now to FIGS. 12A and 12B, a front perspective view of the ES pencil 200 is shown in FIG. 12A with portions of the electrode 214 removed and portions of the nozzle 212 removed. FIG. 12B shows a front view of the ES pencil 200 as depicted in FIG. 12A to illustrate an inside diameter ID2 (FIG. 12B) of the distal portion 212b of the nozzle 212, which is measured within the fluid lumen 220 between inner surfaces of the nozzle 212 where an inside diameter of the distal portion 212b of the nozzle 212 is at a maximum (e.g., adjacent to the proximal portion 212a of the nozzle 212). Also illustrated in FIG. 12B is an area A1 of the distal opening 227 of the fluid lumen 225 extending through the handle housing 210. In the example of FIG. 12B, the inside diameter ID2 is about 0.395 inches and the area A1 of the distal opening 227 is about 0.0341 inches$^2$. Using a value of 0.395 inches for the inside diameter ID2, a maximum area A2 of the fluid lumen 220 can be determined by the equation $3.14(0.395/2)^2$, which gives a result of 0.122 inches$^2$. Thus, a ratio of A1:A2 (e.g., 0.0341/0.122) gives a value of 0.28.

The above-described geometries of each of the examples of FIGS. 5-12B, for an electrode length of about 2.5 inches and an outside diameter OD1 of about 0.322 inches, provide unexpectedly superior electrode visualization and smoke capture performance during operation of the ES pencil 200.

Figures 13, 14:
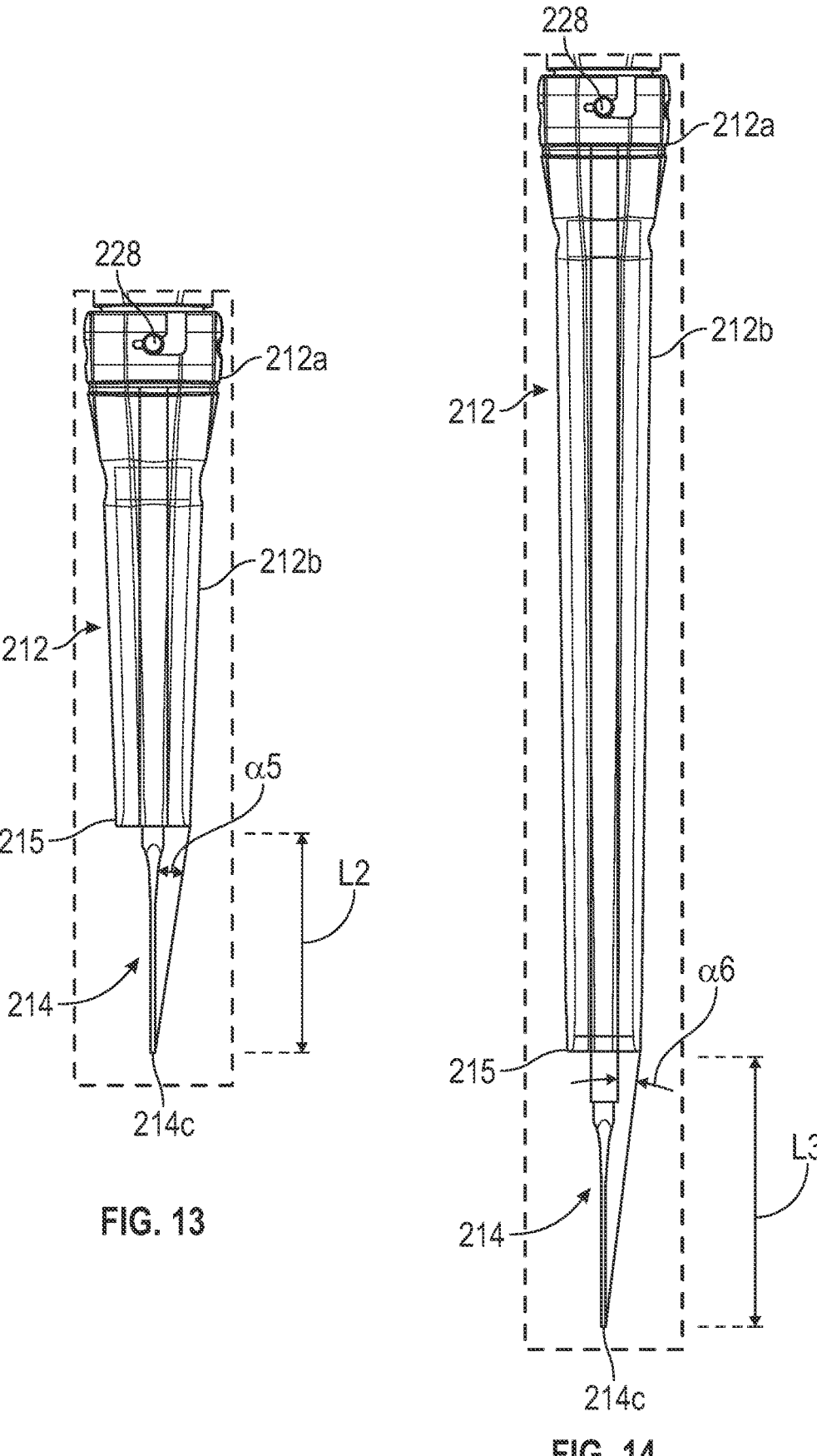
FIGS. 13 and 14 are top views of a portion of the ES pencil of FIG. 2, in accordance with aspects of the disclosure.

Turning now to FIGS. 13 and 14, respective top views of the nozzle 212 and the electrode 214 are shown to illustrate other examples of the ES pencil 200. The examples of FIGS. 13 and 14 are similar to the examples shown in FIGS. 5-12B and will only be described to the extent necessary to identify differences in geometry. In the example shown in FIG. 13, a length of the electrode 214 is about 4.0 inches and the outside diameter OD1 (FIG. 5) of the distal opening 218 of the nozzle 212 is about 0.322 inches. The electrode 214 is shown extending distally past the distal end 215 of the nozzle 212 to expose at least a portion of the electrode 214 from the nozzle 212. A length L2 of the electrode 214 that extends distally past the distal end 215 of the nozzle 212 is measured between the distal tip 214c of the electrode 214 and the distal end 215 of the nozzle 212. In the example shown in FIG. 13, the length L2 is about 0.979 inches. Thus, a ratio of L2:OD1 (e.g., 0.979/0.322) gives a value of 3.0. Also illustrated in FIG. 13 is an angle α5 measured from the distal tip 214c of the electrode 214 to a lateral side of the distal end 215 of the nozzle 212. In the example shown in FIG. 13, the angle α5 is about 8.477 degrees. The above-described geometry of FIG. 13 provides unexpectedly superior electrode visualization and smoke capture performance during operation of the ES pencil 200 for an electrode length of about 4.0 inches and an outside diameter OD1 of about 0.322 inches.

In the example shown in FIG. 14, a length of the electrode 214 is about 6.5 inches and the outside diameter OD1 (FIG. 5) of the distal opening 218 of the nozzle 212 is about 0.322 inches. The entire distal portion 214a of the electrode 214 and at least a portion of the collet 216 are shown extending distally past the distal opening 218 of the nozzle 212 to expose at least a portion of the electrode 214 from the nozzle 212. A length L3 of the electrode 214 that extends distally past the distal end 215 of the nozzle 212 is measured between the distal tip 214c of the electrode 214 and the distal end 215 of the nozzle 212. In the example shown in FIG. 14, the length L3 is about 1.211 inches. Thus, a ratio of L3:OD1 (e.g., 1.211/0.322) gives a value of 3.8. Also illustrated in FIG. 14 is an angle α6 measured from the distal tip 214c of the electrode 214 to a lateral side of the distal end 215 of the nozzle 212. In the example shown in FIG. 14, the angle α4 is about 6.863 degrees. The above-described geometry of FIG. 14 provides unexpectedly superior electrode visualization and smoke capture performance during operation of the ES pencil 200 for an electrode length of about 6.5 inches and an outside diameter OD1 of about 0.322 inches.

Figure 15:
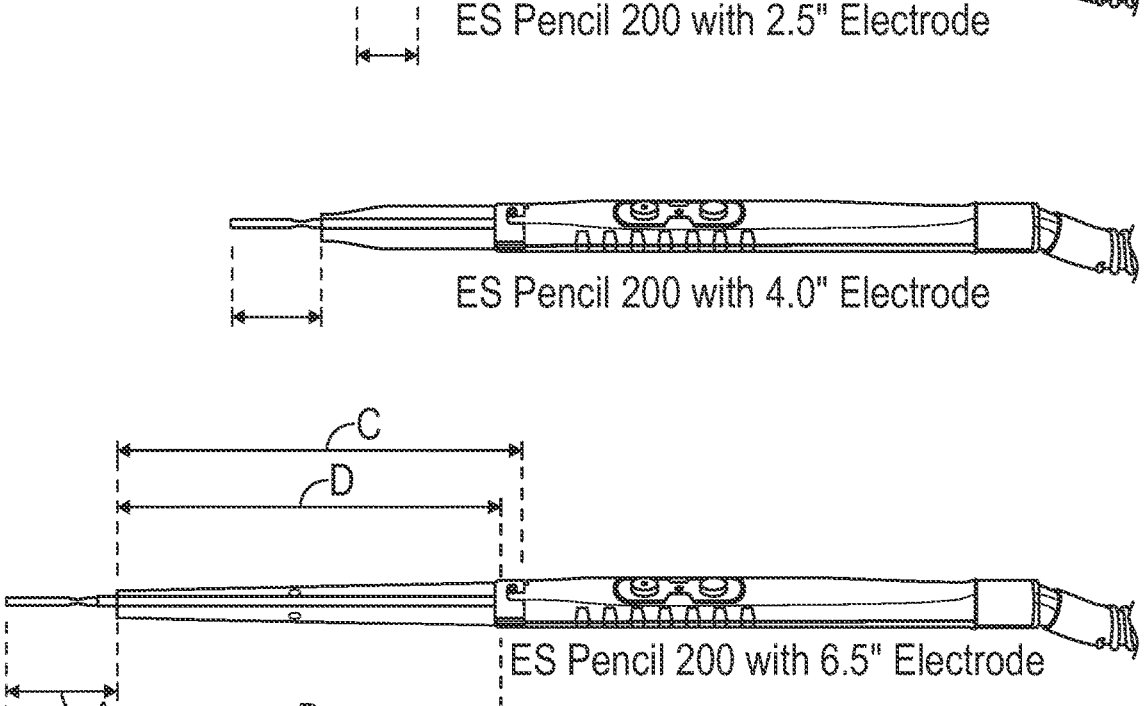
FIG. 15 shows top side views of various examples of the ES pencil of FIG. 2, in accordance with aspects of the disclosure.

FIG. 15 shows a side-by-side comparison of the ES pencil 200 for each of the above-described electrode lengths of about 2.5 inches, about 4.0 inches, and about 6.5 inches to illustrate the differences and similarities in geometry between the three examples. For each of the lengths A-D indicated in FIG. 15, the illustrated values are in inches. For all three illustrated electrode lengths, the shutoff diameter SOD1 (FIG. 8) where the inside diameter of the distal portion 212b of the nozzle 212 is at a minimum is about 0.262 inches and the outside diameter OD1 (FIG. 5) of the distal opening 218 of the nozzle 212 is about 0.322 inches. Length A corresponds to the above-described length L1 of the electrode 214 that extends distally past the distal end 215 of the nozzle 212 and is measured between the distal tip 214c of the electrode 214 and the distal end 215 of the nozzle 212. Length B is measured between the distal tip 214c of the electrode 214 and the distal end 229 of the handle housing 210. Length C is a total length of the nozzle 212 measured between the proximal end 211 of the nozzle 212 and the distal end 215 of the nozzle 212. Length D is measured between the distal end 215 of the nozzle 212 and the distal end 229 of the handle housing 210. Also illustrated for each of the three electrode lengths is a ratio of length D:length A. By way of example, the ratio of length D:length A for an electrode length of about 2.5 inches is calculated as 0.955/0.65, which gives a result of 1.469.

Figure 16:
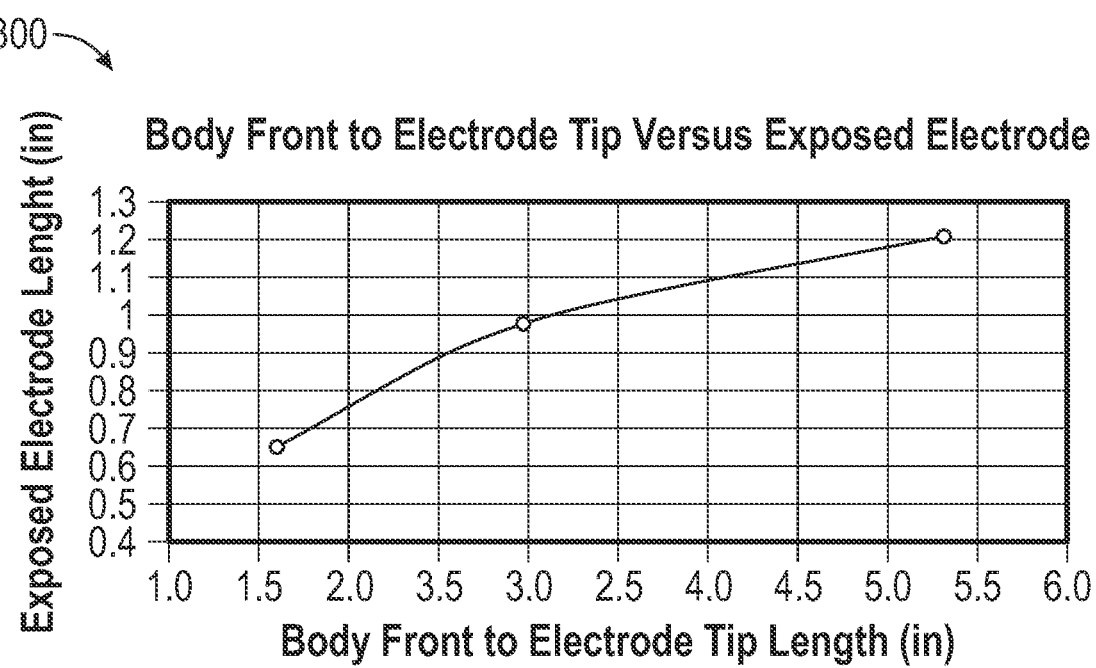
FIGS. 16-18 show various plots to illustrate the relationship between the dimensions and geometry of various examples of the ES pencil of claim 2, in accordance with aspects of the disclosure.
Figure 17:
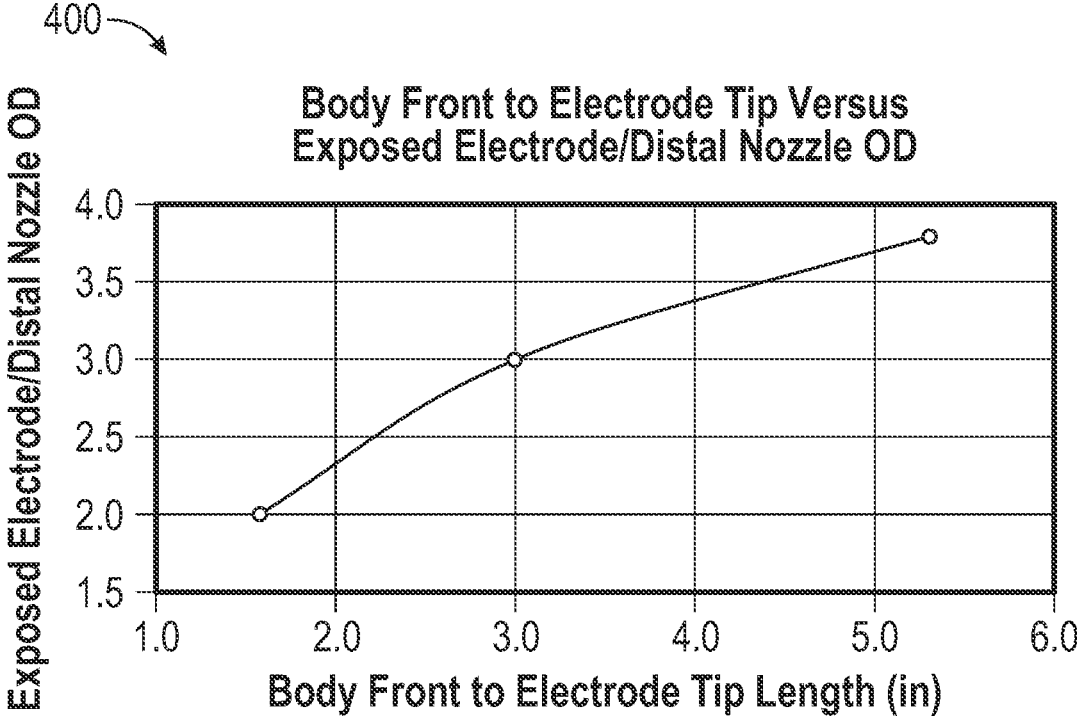
Figure 18:
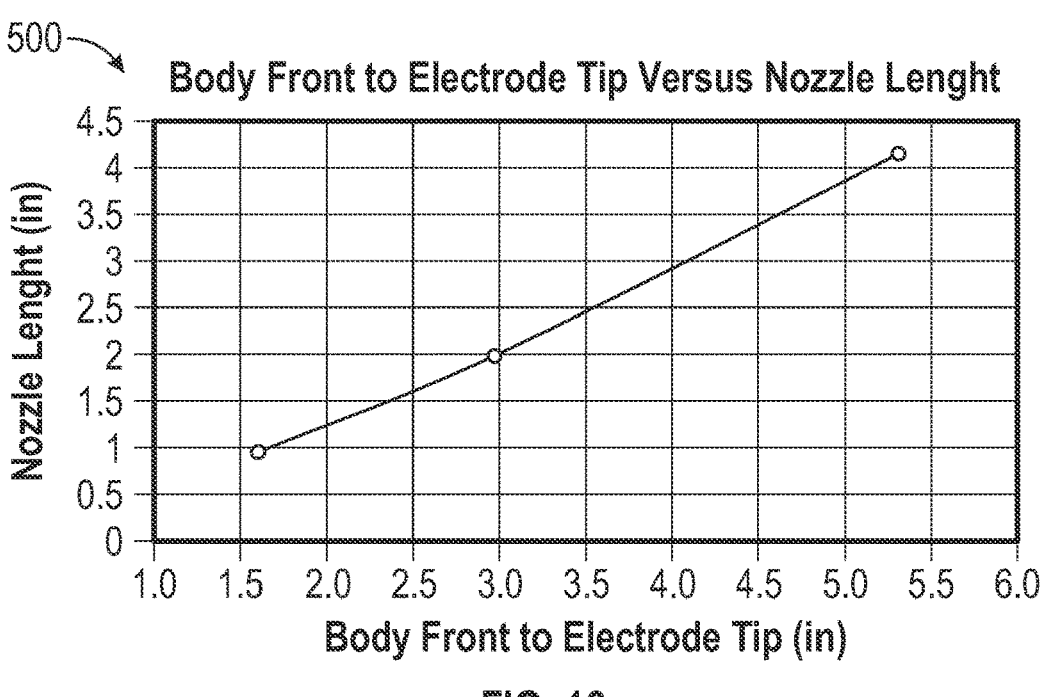

Referring now to FIGS. 16-18, a series of plots are shown to illustrate how various geometries and geometrical ratios related to the ES pencil 200 change as a function of length B measured between the distal tip 214c of the electrode 214 and the distal end 229 of the handle housing 210. Referring initially to FIG. 16, a plot 300 illustrating length A as a function of length B is shown. For example, for a length B of about 5.361 inches, length A is about 1.211 inches, which corresponds to lengths A and B for an electrode length of about 6.5 inches as indicated in FIG. 15. From the plot of FIG. 16, values for length B corresponding to electrode lengths other than the examples illustrated in FIG. 15 can be derived. For example, for a length B of about 2.0 inches, length A is about 0.75 inches and this would correspond to an electrode length within a range between about 2.75 inches and about 3.50 inches.

FIG. 17 illustrates a plot 400 of a ratio of length A:OD1 as a function of length B. As indicated above, OD1 is the outside diameter of the distal opening 218 of the nozzle 212 and is about 0.322 inches for each of the examples shown in FIG. 15. By way of example, for a length B of about 2.969 inches, the ratio of length A:OD1 is about 3.0. In this example, a length B of about 2.969 inches corresponds to length B for an electrode length of 4.0 inches. FIG. 18 illustrates a plot 500 of length C as a function of length B. By way of example, for a length B of about 1.605 inches, length C is about 1.183 inches, which corresponds to lengths B and C for an electrode length of about 2.5 inches as indicated in FIG. 15. By way of another example, for a length B of about 5.0 inches, length C is about 3.8 inches.

As detailed below, the above-specified dimensions and geometries of the various examples of the ES pencil 200 described above with respect to FIGS. 5-18 have been shown, through rigorous smoke capture testing, to provide unexpectedly superior electrode visualization and smoke capture performance of the ES pencil 200. Using the surgical smoke evacuation system 100 of the present disclosure with an electrosurgical generator for delivering electrosurgical energy to the ES pencil 200, smoke capture testing was performed under specific protocols to measure the percentage of smoke captured by the ES pencil 200. To measure smoke evacuation performance on real tissue during simulated use, the tissue is placed in an isolation box and simulated tissue cutting procedures are performed using the ES pencil 200 to develop a smoke plume that is measured by an air particle counter. Two different approaches are used to allow for a quantitative measure of smoke evacuation performance, one approach specific to the tissue cutting modality and one approach specific to the tissue coagulation modality. For both modalities, electrosurgical energy is delivered to the tissue at about 30 Watts of power. The smoke plume measurement is performed first with the smoke evacuator 130 turned off and then again with the smoke evacuator 130 turned on. The percentage of smoke capture for the ES pencil 200 is determined by comparing the concentration of particular matter 2.5 (PM2.5) without smoke evacuation (e.g., with smoke evacuator 130 turned off) to the concentration of PM2.5 with smoke evacuation (e.g., with smoke evacuator 130 turned on). As is known in the art, PM2.5 describes fine inhalable particles with diameters that are 2.5 micrometers or less.

The test process includes initially measuring PM2.5 levels within the isolation box to obtain a first baseline value (baseline A) of PM2.5 levels within the isolation box. After the baseline A is obtained, and with the smoke evacuator 130 turned off, PM2.5 levels within the isolation box are measured while the ES pencil 200 is caused to cut the tissue. Once a sufficient number of tissue cuts have been completed, the isolation box is vacuumed using a secondary suction unit. To ensure the isolation box has been properly evacuated using the secondary suction unit, PM2.5 levels are again measured within the isolation box to obtain a second baseline value (baseline B) of PM2.5 levels within the isolation box. After the baseline B is obtained, and with the smoke evacuator 130 turned on, PM2.5 levels within the isolation box are measured while the ES pencil 200 is caused to cut the tissue. Once a sufficient number of tissue cuts have been completed, the isolation box is again vacuumed using the secondary suction at the conclusion of the testing process. To determine the percentage of smoke captured by the ES pencil 200 under testing, the following formula is used:

$$\% \text{ Capture} = \frac{\begin{array}{c}(\text{Average } PM2.5 \text{ Burden Without } Evac \text{ across all samples}) - \\ PM2.5 \text{ Burden With } Evac)\end{array}}{(\text{Average } PM2.5 \text{ Burden Without } Evac \text{ across all samples})} * 100$$

wherein:
the burden is defined as the PM2.5 level of each tissue cut minus baseline PM2.5 levels;
PM2.5 Burden without evacuation=PM2.5 without evacuation−Baseline A PM2.5; and
PM2.5 Burden with evacuation=PM2.5 with evacuation−Baseline B PM2.5.

Applying the above-described testing process to the ES pencil 200 of this disclosure, the smoke capture percentage achieved was about 90% using a setting of about 60% power on the smoke evacuator 130 and about 99%+using a setting of about 100% power on the smoke evacuator 130.

Figure 19:
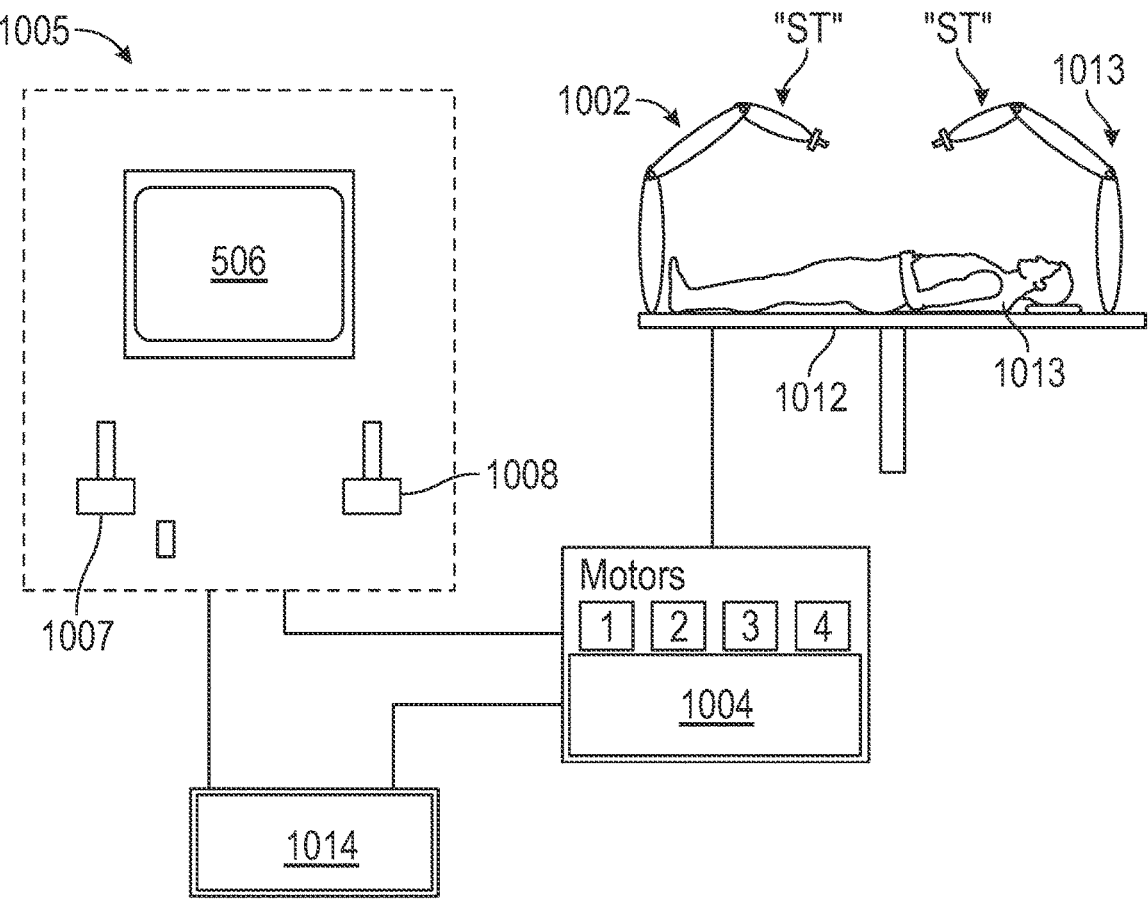
FIG. 19 is a schematic illustration of an exemplary robotic surgical system configured for use with the present disclosure.

Turning now to FIG. 19, a robotic surgical system 1000 configured for use in accordance with this disclosure is shown. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." The surgical tools "ST" may include, for example, the ES pencil 200 of the present disclosure, thus providing any of the above-detailed functionality on a robotic surgical system 1000.

Robot arms 1002, 1003 may be driven by electric drives, e.g., motors, connected to control device 1004. The motors, for example, may be rotational drive motors configured to provide rotational inputs to accomplish a desired task or tasks. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Control device 1004, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided. Alternatively or additionally, control device 1004 may control one or more of the motors based on torque, current, or in any other suitable manner.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. An electrosurgical pencil, comprising:
   a handle housing having a proximal end portion and a distal end portion, the handle housing defining a fluid lumen and a central longitudinal axis;
   a nub protruding from an exterior surface of the distal end portion of the handle housing;
   a nozzle defining a fluid lumen in fluid communication with the fluid lumen defined by the handle housing for evacuating fluid from a surgical site, wherein the nozzle includes a slot configured to receive the nub to releasably couple the nozzle to the handle housing; and
   an electrode configured to deliver electrosurgical energy to tissue, the electrode having a proximal portion coupled to the handle housing and a distal portion extending through the fluid lumen defined by the nozzle such that at least a portion of the electrode extends distally from a distal end of the nozzle, the electrode defining a central longitudinal axis offset from the central longitudinal axis defined by the handle housing by about 0.042 inches.

2. The electrosurgical pencil according to claim 1, wherein a ratio between a first length measured between a distal end of the handle housing and the distal end of the nozzle and a second length measured between the distal end of the nozzle and a distal end of the electrode is about 1.469.

3. The electrosurgical pencil according to claim 1, wherein the distal end portion of the handle housing is recessed relative to the rest of the handle housing.

4. The electrosurgical pencil according to claim 1, wherein a length between a distal tip of the electrode and the distal end of the nozzle is about 0.65 inches.

5. The electrosurgical pencil according to claim 1, wherein the electrode is about 2.5 inches in length.

6. The electrosurgical pencil according to claim 1, wherein the fluid lumen defined by the handle housing includes a distal opening in fluid communication with the fluid lumen defined by the nozzle, and a ratio between an area of the distal opening and a maximum area of the fluid lumen defined by the nozzle is about 0.28.

7. The electrosurgical pencil according to claim 1, wherein a ratio between a length measured between a distal tip of the electrode and the distal end of the nozzle and an outside diameter of the distal end of the nozzle is about 2.0.

8. The electrosurgical pencil according to claim 1, wherein an inner diameter of the nozzle at the distal end of the nozzle is about 0.304 inches.

9. The electrosurgical pencil according to claim 1, wherein an outside diameter of the distal end of the nozzle is about 0.322 inches.

10. The electrosurgical pencil according to claim 1, wherein the electrode is removably received through a collet having a flange disposed within the fluid lumen defined by the nozzle, and a ratio between an area of the flange and an area of the fluid lumen defined by the nozzle at the flange is about 0.36.

11. The electrosurgical pencil according to claim 1, wherein at least a portion of the nozzle is formed from a radiopaque material.

12. The electrosurgical pencil according to claim 1, wherein a ratio between a distance by which the central longitudinal axis defined by the electrode is offset from the central longitudinal axis defined by the handle housing and an outside diameter of the distal end of the nozzle is about 0.13.

13. The electrosurgical pencil according to claim 1, wherein a length between a distal end of the handle housing and a distal tip of the electrode is about 1.065 inches.

14. An electrosurgical pencil, comprising:
   a handle housing defining a fluid lumen and a central longitudinal axis;
   a nozzle removably coupled to a distal end portion of the handle housing, the nozzle defining a fluid lumen in fluid communication with the fluid lumen defined by the handle housing for evacuating fluid from a surgical site;
   an electrode configured to deliver electrosurgical energy to tissue and extending through the fluid lumen defined by the nozzle;
   a collet coupled to the handle housing and configured to be removably coupled to the electrode, the collet having a flange disposed within the fluid lumen defined by the nozzle, wherein a ratio between an area of the flange and an area of the fluid lumen defined by the nozzle at the flange is about 0.36; and
   at least one activation button extending from a top side of the handle housing and configured to control delivery of electrosurgical energy to the electrode, wherein the electrode defines a central longitudinal axis offset from the central longitudinal axis defined by the handle housing toward the top side of the handle housing.

15. The electrosurgical pencil according to claim 14, wherein the fluid lumen defined by the handle housing includes a distal opening in fluid communication with the fluid lumen defined by the nozzle, the distal opening having an area of about 0.0341 inches$^2$.

16. The electrosurgical pencil according to claim 14, wherein a ratio between a first length measured between a distal end of the handle housing and a distal end of the nozzle and a second length measured between the distal end of the nozzle and a distal end of the electrode is about 1.469.

17. The electrosurgical pencil according to claim 14, wherein a proximal portion of the nozzle includes a slot configured to receive a nub protruding from the distal end portion of the handle housing to releasably couple the nozzle to the handle housing.

18. The electrosurgical pencil according to claim 14, wherein a ratio between a distance by which the central longitudinal axis defined by the electrode is offset from the central longitudinal axis defined by the handle housing and an outside diameter of a distal end of the nozzle is about 0.13.

19. An electrosurgical pencil, comprising:

a handle housing defining a fluid lumen and a central longitudinal axis, the handle housing having a distal end portion that is recessed relative to the rest of the handle housing;

a nub protruding from an exterior surface of the distal end portion of the handle housing;

a nozzle removably coupled to the recessed distal end portion of the handle housing, the nozzle defining a fluid lumen in fluid communication with the fluid lumen defined by the handle housing for evacuating fluid from a surgical site, the nozzle having a proximal end portion defining a slot configured to receive the nub to removably couple the nozzle to the handle housing; and an electrode configured to deliver electrosurgical energy to tissue, the electrode having a proximal portion coupled to the handle housing and a distal portion extending through the fluid lumen defined by the nozzle such that at least a portion of the electrode extends distally from a distal end of the nozzle, wherein a length between a distal tip of the electrode and the distal end of the nozzle is about 0.65 inches.

* * * * *